United States Patent [19]
de la Brousse et al.

[11] Patent Number: 5,698,389
[45] Date of Patent: Dec. 16, 1997

[54] TRANSCRIPTIONAL PROMOTER OF THE MURINE OBESITY GENE

[75] Inventors: Fabienne Charles de la Brousse, San Francisco; Jin-long Chen, Millbrae, both of Calif.

[73] Assignee: Tularik, Inc., South San Francisco, Calif.

[21] Appl. No.: 558,545

[22] Filed: Nov. 16, 1995

[51] Int. Cl.$^6$ .............. C12N 5/10; C12N 15/11; C12Q 1/00
[52] U.S. Cl. .............. 435/4; 435/325; 536/23.1; 536/24.1
[58] Field of Search ............. 536/24.1, 23.1; 435/6, 325, 4

[56] References Cited

FOREIGN PATENT DOCUMENTS

WO96/29405  9/1996  WIPO .

OTHER PUBLICATIONS

He et al., The Journal of Biological Chemistry 270(48):28887–28891 (1995).

Miller et al., Proc. Natl. Acad. Sci. USA 93(11):5507–5511 (1996).

Zhang et al., Nature 372:425–432 (1994).

Primary Examiner—George C. Elliott
Assistant Examiner—Johnny F. Railey, II
Attorney, Agent, or Firm—Richard Aron Osman

[57] ABSTRACT

The invention relates to the Ob gene transcriptional promoter. The subject promoters generally comprise a C/EBP binding site and a novel untranslated Ob gene exon. Ob gene promoters are used in diagnosis and pharmaceutical development. In particular, transfected adipocytes comprising Ob gene promoters operably linked to a reporter are used in high-throughput pharmaceutical screens.

7 Claims, 7 Drawing Sheets

Mouse *ob* Gene

Asp718
↓

| | |
|---|---|
| GGTACCAAAGGAAGACAAGTTGCCCTGAGCTTGGGACCAGTTTCTCCTCT | -409 |
| GAGCAGCCAGGTTAGGTATGCAAAGAGCTGTCGGAAAAAGCAGCTGGCAG | -359 |
| AGTCCTGGCTCACTGGTCTCCCTGTCCCCAAGCCAGCCTTCTGTAGCCTC | -309 |
| TTGCTCCCTGCGGTGCTGGAAGCACCATCCCAAGGGACCCGTCCTTAAAC | -259 |
| TACCGCTGCTCAGTAGCTGCTGGCCGGACCTCGAGGATTACCGGCTCATA | -209 |
| CCAAGCGCCCCCAAACTTGCACTCGAGGGCGCGGCTGAAGTTCTCCCTCG | -159 |
| AGGCGCCTAGAATGGAGCACTAGGTTGCTGCTGCCACTGTTGCTGGCCCG | -109 |
| CTGGGTGGGGCGGGAGTTGGCGCTCGCAGGGACTGGGGCTGGCCGGACAG | -59 |
| TTGCGCAAGTGGCACTGGGGCAGT TATAA GAGGGGCAGGCAGGCATGGAG | -9 |
| CCCCGGAGGGATCCCTGCTCAGCAGCTGCAAG GTAAGGCCCGGGGCGCG | +42 |
| +1 | |
| CTACTTTCTCCTCCACCAGTCTTTCTAATAGCACCCCATCCAGCTCTGGA | +92 |
| | EcoRI ↓ |
| AATTAGAGAAACTGAGGCAAGAAGGAGGTCATGTGGACAGCTTGGTGTTG | +142 |
| AATTC | +147 |

FIGURE 1(C)

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
  ( A ) LENGTH: 606 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:1:

```
GGTACCAAAG GAAGACAAGT TGCCCTGAGC TTGGGACCAG TTTCTCCTCT GAGCAGCCCA    60

GGTTAGGTAT GCAAAGAGCT GTCGGAAAAA GCAGCTGGCA GAGTCCTGGC TCACTGGTCT   120

CCCTGTCCCC AAGCCAGCCT TCTGTAGCCT CTTGCTCCCT GCGGTGCTGG AAGCACCATC   180

CCAAGGGACC CGTCCTTAAA CTACCGCTGC TCAGTAGCTG CTGGCCGGAC CTCGAGGATT   240

ACCGGCTCAT ACCAAGCGCC CCCAAACTTG CACTCGAGGG CGCGGCTGAA GTTCTCCCTC   300

GAGGCGCCTA GAATGGAGCA CTAGGTTGCT GCTGCCACTG TTGCTGGCCC GCTGGGTGGG   360

GCGGGAGTTG GCGCTCGCAG GGACTGGGGC TGGCCGGACA GTTGCGCAAG TGGCACTGGG   420

GCAGTTATAA GAGGGGCAGG CAGGCATGGA GCCCGGAGG GATCCCTGCT CCAGCAGCTG   480

CAAGGTAAGG CCCGGGGCGC GCTACTTTCT CCTCCACCAG TCTTTCTAAT AGCACCCCAT   540

CCAGCTCTGG AAATTAGAGA AACTGAGGCA AGAAGGAGGT CATGTGGACA GCTTGGTGTT   600

GAATTC                                                              606
```

( 2 ) INFORMATION FOR SEQ ID NO:2:

( i ) SEQUENCE CHARACTERISTICS:

( A ) LENGTH: 10 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

GTTGCGCAAG 10

( 2 ) INFORMATION FOR SEQ ID NO:3:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

GGATCCCTGC TCCAGCAGCT GCAAG 25

( 2 ) INFORMATION FOR SEQ ID NO:4:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:4:

AATGTGCTGG AGACCCCTGT G 21

( 2 ) INFORMATION FOR SEQ ID NO:5:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

CTTCAGCATT CAGGGCTAAC ATCCAACTGT 30

( 2 ) INFORMATION FOR SEQ ID NO:6:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

AGGTCATTGG CTATCTGCAG CACA 24

( 2 ) INFORMATION FOR SEQ ID NO:7:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

AGCCACAGGA ACCGACACAG GGGTCTCCAG CACATT 36

( 2 ) INFORMATION FOR SEQ ID NO:8:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

ATAGGCACTG CTTGAACATA AGACAGATAG GACCAA 36

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CCGAATTCGC CCAGGAATGA AGTCCAAGCC 30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

CCGAATTCCG CCAGTGACCC TCTGCTTGGC 30

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CCACGCGTCT GCTCCAGCAG CTGCA 25

( 2 ) INFORMATION FOR SEQ ID NO:12:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CCGCGGCCGC GCACACTGCT TGCTCTTCCA G 31

( 2 ) INFORMATION FOR SEQ ID NO:13:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:13:

CCGAATTCCT GCAGCTGTGG GAAACCTAAC CATCTC      36

( 2 ) INFORMATION FOR SEQ ID NO:14:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:14:

GCGAATTCGG      10

TRANSCRIPTIONAL PROMOTER OF THE MURINE OBESITY GENE

FIELD OF THE INVENTION

The field of this invention is the transcriptional promoter of the Obesity gene and its use in drug screening.

BACKGROUND

Satiety in vertebrates is controlled by a blood-borne hormone encoded by the obesity (Ob) gene (1). Homozygous recessive mutations of the Ob gene (ob/ob) lead to the gross expansion of adipose tissue. Since animals lacking a functional Ob gene become phenotypically obese, it has been predicted that the Ob gene product plays a central role in energy homeostasis and appetite suppression.

The Ob gene has recently been cloned, facilitating molecular characterization of its encoded protein (2). The Ob gene product, termed leptin, is a secreted polypeptide produced by adipose tissue. Fat tissue accumulates in response to the intake of excess energy stores, becoming grossly expanded in animals lacking either functional leptin or its putative receptor (3). Under such circumstances, expression of the Ob gene is markedly elevated (2, 4). These observations give evidence of a feedback loop responsible for controlling vertebrate energy balance. Adipose tissue subsides under conditions of food deprivation, resulting in a reduced level of leptin production and a corresponding increase in appetite. In the well-fed state, excess energy stores accumulate in adipose tissue. Upon maturation and expansion, adipocytes activate expression of the Ob gene, whose product then serves to quell satiety and stimulate metabolic activity.

Several lines of evidence have indicated that leptin production may be regulated at the level of transcription of its encoding gene. Friedman and colleagues (2) reported that adipose tissue derived from homozygous Ob-defective animals contains appreciably higher levels of leptin mRNA than that of either heterozygous or wild-type controls. Similar observations have been made using mice bearing homozygous recessive mutations in the Db gene—which has been predicted to encode the leptin receptor (4). Increased levels of Ob mRNA have also been observed in obese humans (5, 6). Finally, several recent papers have provided evidence that expression of the Ob gene is elevated in response to insulin and other blood borne hormones involved in energy homeostasis (7, 8, 9). These observations provide evidence that transcription of the Ob gene is sensitively balanced with respect to the supply of metabolic energy stores as well as the hormonal factors responsible for controlling energy homeostasis. In order to initiate studies of the molecular events controlling Ob gene expression, we have cloned the promoter of the mouse Ob gene and performed studies regarding its function.

CITED LITERATURE

1. Coleman, D. L. (1973) *Diabetologia* 9, 294–298.
2. Zhang, Y., et al. (1994) *Nature* 372, 425–432.
3. Coleman, D. L. (1978) *Diabetologia* 14, 141–148.
4. Maffei, M., et al. (1995) *Proc. Natl. Acad. Sci. USA* 92, 6957–6960.
5. Lönnquist, F., et al. (1995) *Nature Medicine* 9, 950–953.
6. Hamilton, B. S., et al. (1995) *Nature Medicine* 9, 953–956.
7. De Vos, P., Saladin, R., Auwerx, J. & Staels, B. (1995) *J. Biol. Chem.* 270, 15958–15961.
8. MacDougald, O. A., et al. (1995) *Proc. Natl. Acad. Sci. USA* 92, 9034–9037.
9. Saladin, R., et al. (1995) *Nature* 377, 527–529.
10. Sambrook, J., Fritsch, E. F. & Maniatis, T. (1989) *Molecular Cloning: A Laboratory Manual* 2nd ed. (Cold Spring Harbor Laboratory Press, Cold Spring Harbor, N.Y.).
11. Rodbell, M. (1964) *J. Biol. Chem.* 239, 375–380.
12. Rolland, V., et al. (1995) *J. Biol. Chem.* 270, 1102–1106.
13. Graham, F. L. & Van der Eb, A. J. (1973) *Virology* 52, 456–457.
14. Dignam, J. D., et al. (1983) *Nucleic Acids Res.* 11, 1475–1489.
15. Shuman, J. D., Vinson, C. R. & McKnight, S. L. (1990) *Science* 249, 771–774.
16. Cao, Z., Umek, R. M. & McKnight, S. L. (1991) *Genes Dev.* 5, 1538–1552.
17. Yeh, W-C., Cao, Z., Classon, M. & McKnight, S. L. (1995) *Genes Dev.* 9, 168–181.
18. Zhang, Y., et al. (1995) *Nature* 374, 479.
19. Breathnach, R. & Chambon, P. (1981) *Ann. Rev. Biochem.* 50, 349–383.
20. Yeh, W-C. & McKnight, S. L. (1995) *Proc. Natl. Acad. Sci.* in press.
21. Friedman, A., Landschulz, W. & McKnight, S. L. (1989) *Genes Dev.* 3, 1314–1322.
22. Ossipow, V., et al. (1993) *Proc. Natl. Acad. Sci. USA* 90, 8219–8223.

SUMMARY OF THE INVENTION

The invention provides methods and compositions relating to the Ob gene transcriptional promoter. The subject promoters generally comprise a C/EBP binding site and may include a novel untranslated Ob gene exon. An exemplary novel Ob C/EBP binding site and novel 5' untranslated Ob gene exons are disclosed.

The subject nucleic acids find a variety of uses including uses in diagnosis and pharmaceutical development. In particular, hybridization probes and PCR primers derived from the disclosed promoters are used to identify genetic mutations in samples comprising an Ob gene. Additionally, transfected adipocytes comprising the subject promoters operably linked to a reporter are used in high-throughput pharmaceutical screens. In addition, the promoters are also used in direct binding assays with DNA binding proteins such as C/EBP.

(A)-1, -2 Primer extension mapping of the Ob gene transcription start site. $^{32}$P-labeled FCT151 and FCT152 oligonucleotide primers were annealed to mouse C57BL/6J ob/ob fat mRNA and yeast tRNA, extended with reverse transcriptase, and the products resolved on a denaturing polyacrylamide gel alongside a $^{32}$P-labeled size marker.

(B) Nucleotide sequence (SEQ ID NO:1) of the region surrounding exon1 (−458 to +147) of the mouse Ob gene. This region is flanked by Asp718 and EcoRI restriction sites as indicated. Double underline indicates exon1 sequence. The location of transcription initiation is marked as position +1. The TATA element is boxed and the putative C/EBP binding site (positions −49 to −59) is underlined.

(C) Structure of the Ob gene. Sequencing and restriction mapping analyses of overlapping genomic clones λmob3, a long distance PCR amplicon, and λmob1 were used to generate the map shown. HindIII (H) and BamHI (B) restriction sites are indicated. The −7 kb EcoRI site (R) used in the promoter deletion analysis is also indicated; The * indicates that it is not unique within the 24 kb genomic clone. Solid boxes represent noncoding exon sequences. Stippled boxes represent coding regions of mouse Ob.

Figures 1, 1A:
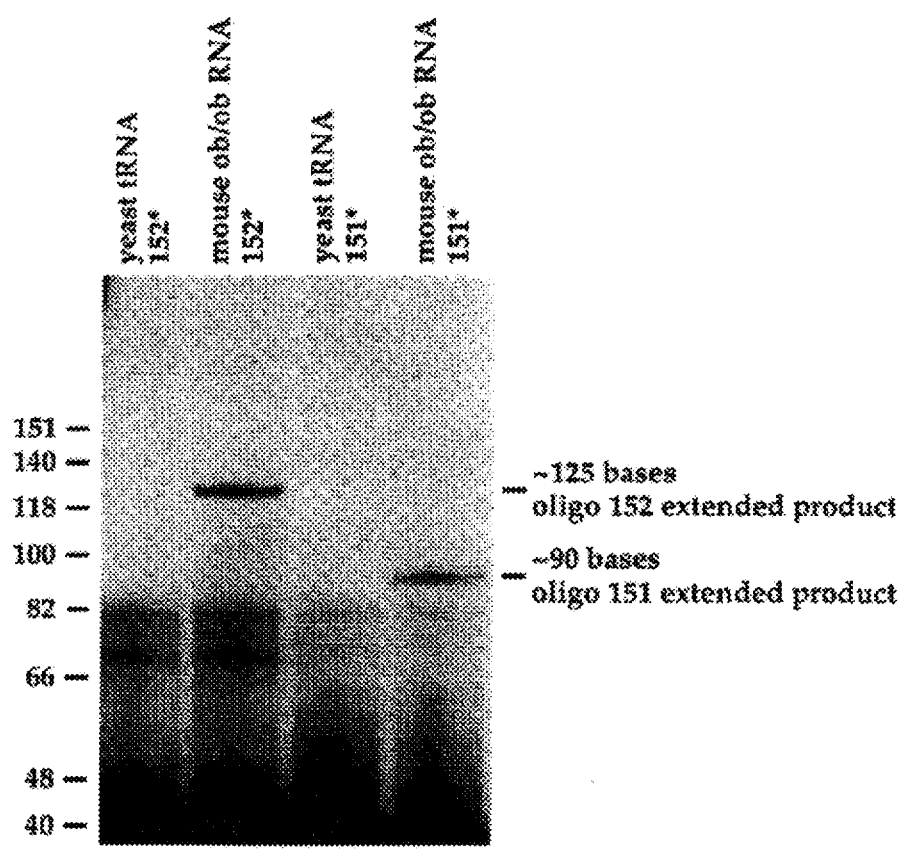
FIGS. 1(A)-1, (A)-2, (B) and (C). Molecular organization of the mouse Ob gene.
Figures 1, 1A, 2:
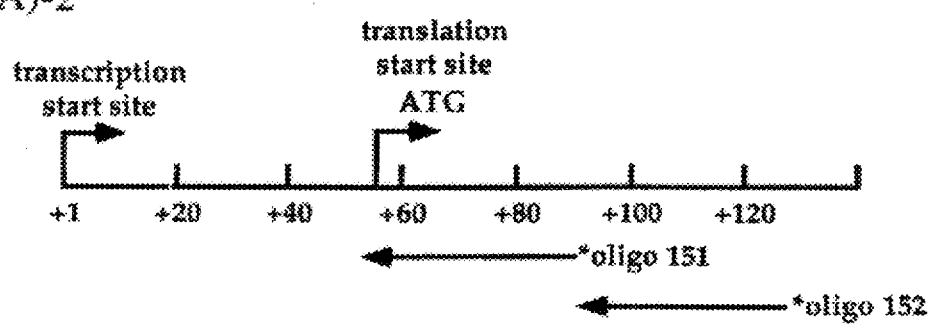

FIG. 2. Expression of luciferase enzymatic activity driven by the mouse Ob promoter in transfected adipocytes.

Isolated adipocytes from mouse epididymal fat pads were transfected by electroporation with: (i) a construct containing a 482 bp fragment (−458 to +24) of the Ob gene promoter fused to luciferase reporter; (ii) a construct bearing a site directed mutation in the putative C/EBP response element; and (iii) promoter-less reporter plasmid. Cells were harvested 18 hours posttransfection and assayed for luciferase activity.

Figure 3A:
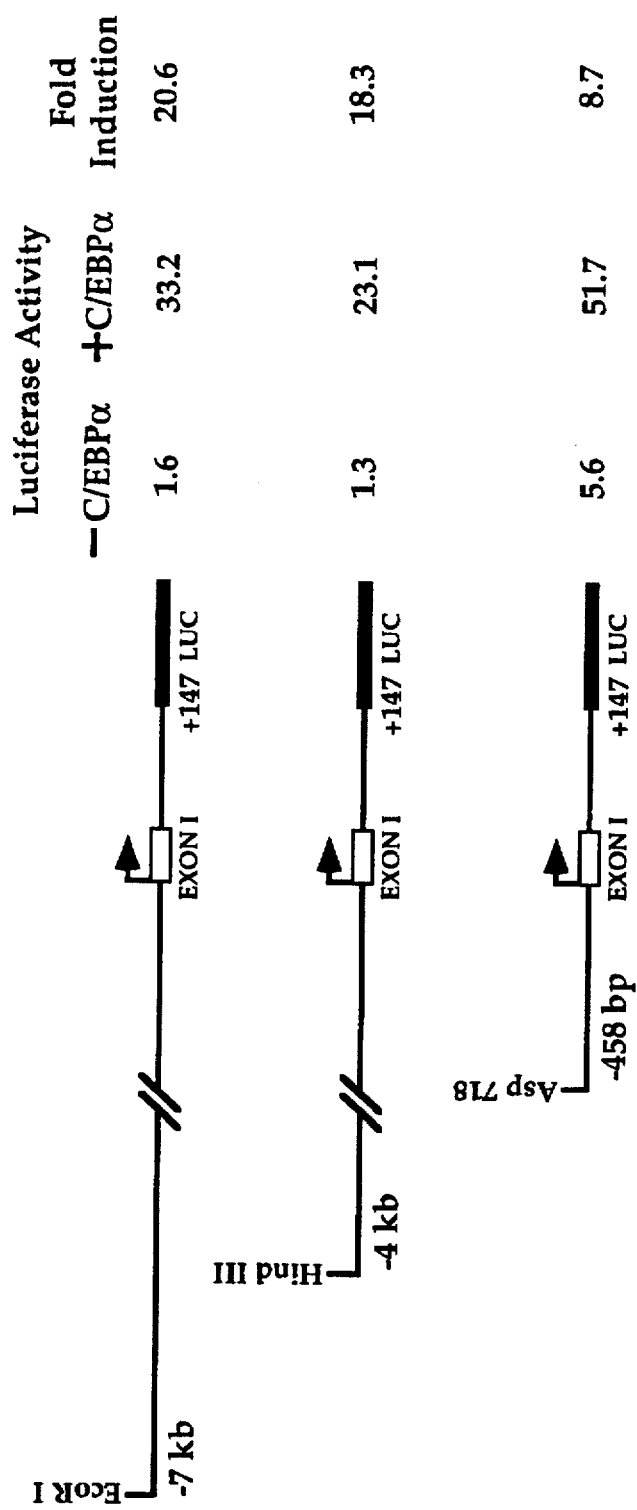

FIGS. 3(A), (B) and (C). Activation of the mouse Ob promoter by C/EBPα.

(A) three Ob promoter/luciferase constructs, generated by restriction enzymes (EcoRI, −7 kb/+147 bp; HindIII, −4 kb/+147 bp; and Asp718, −458 bp/+147 bp) were used in the C/EBPα response assay. 5 μg fo the three different Ob promoter luciferase constructs were cotransfected, respectively, into human HepG2 cells with either 2 μg of an MSV driven C/EBPα expression plasmid (+C/EBPα) or the MSV control plasmid (−C/EBPα). 0.2 μg of a CMV driven β-galactosidase control plasmid was included in all transfection experiments. Luciferase activity was measured after normalized to β-galactosidase activity.

(B) 5' deletion series of Ob-luciferase constructs and the site-directed C/EBP mutation construct were cotransfected into HepG2 cells with the MSV-C/EBPα plasmid. Luciferase activity specified by the Δ1 construct was set to 100, and relative luciferase activities to Δ1 are shown.

(C) Gel mobility shift analysis of adipocyte nuclear extracts on the C/EBP binding site of the Ob promoter. $^{32}$P-end-labeledoligonucleotides sorresponding to residue −64 to −54 of the Ob gene promoter (lanes 1–5), a mutated C/EBP binding site used in transfection assays (lane 6) or an optimal C/EBP binding site (lanes 7 and 8) were incubated with 2 μg of nuclear extract from primary adipocytes (lane 2, 3, 4, and 6–8). In lanes 3, 4, and 8 antiserum directed against C/EBPα was added (α). Preimmune serum (PI) was used in a reaction shown in lane 5.

DETAILED DESCRIPTION OF THE INVENTION

Figure 1B:
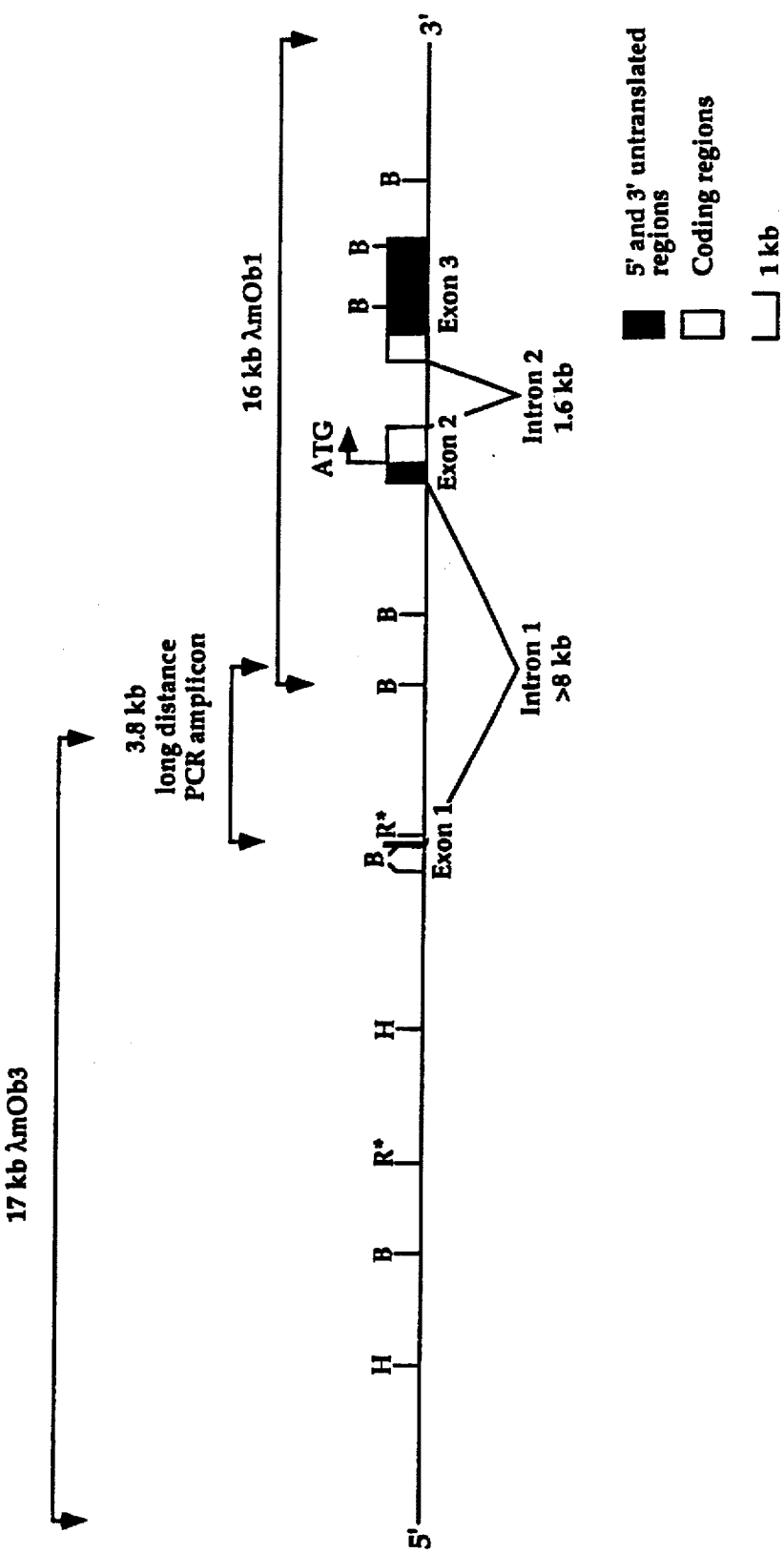
Figure 2:
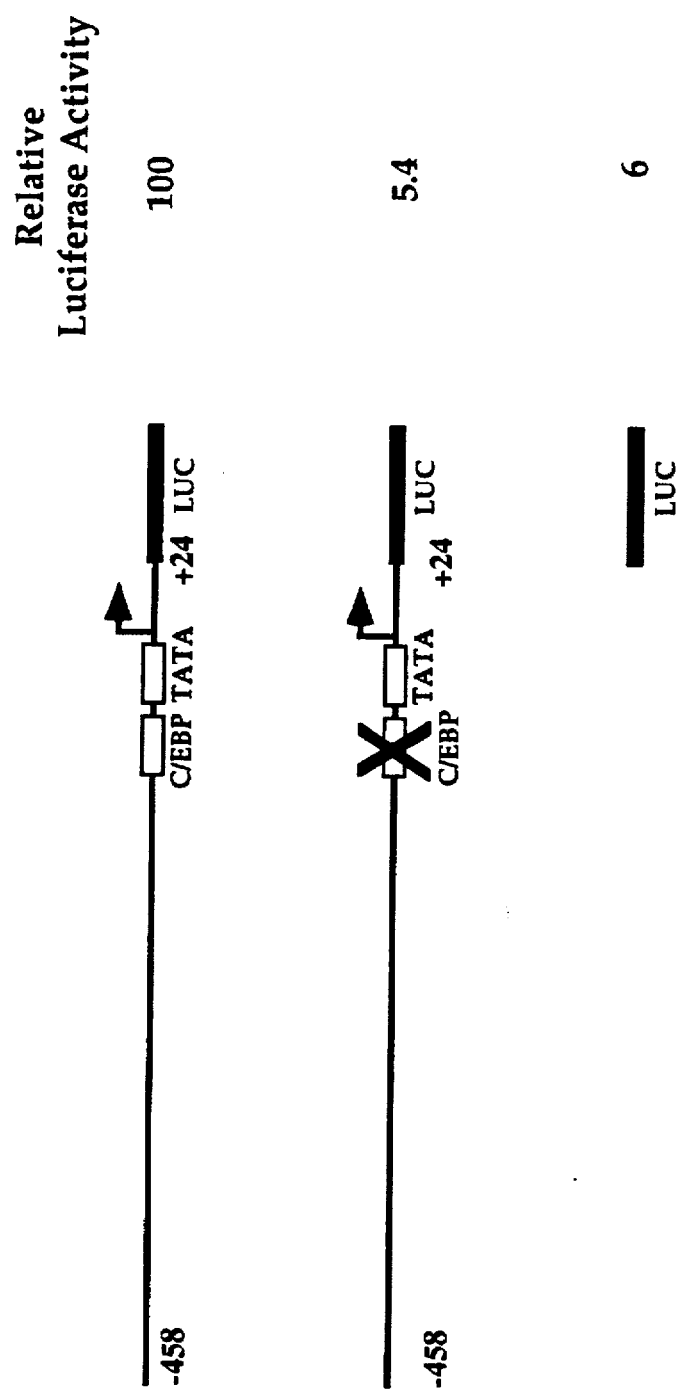

An Ob gene promoter sequence is set out in FIG. 1B. An Ob gene promoter is structurally and functionally defined as a nucleic acid comprising a sequence naturally located 5' and proximate to an Ob structural gene which sequence naturally cis-regulates the transcription of the Ob structural gene, preferably in a C/EBP dependent manner, and which promoter is capable of cis-regulating transcription, preferably in a C/EBP dependent manner. As such, an Ob gene promoter may comprise less than all natural 5' cis-regulatory sequences of a natural Ob gene, so long as the given Ob gene promoter is, in fact, capable of providing a natural cis-regulation of Ob transcription. For example, the experiments disclosed below demonstrate that the Ob gene promoter designated Δ9 and comprising a particular 10 base-pair C/EBP binding site constitutes an effective Ob gene promoter.

Prefered promoters are capable of hybridizing under low stringency conditions with a nucleic acid comprising at least the C/EBP binding site of the Ob promoter of FIG. 1B: GTTGCGCAAG (SEQ ID NO:2), preferably where the low stringency conditions comprise a hybridization buffer comprising 0% formamide in 0.9M saline/0.09M sodium citrate (SSC) buffer at a temperature of 37° C. and remaining bound when subject to washing at 42° C. with the SSC buffer at 37° C., and more preferably where the low stringency conditions comprise a hybridization buffer comprising 20% formamide in 0.9M saline/0.09M sodium citrate (SSC) buffer at a temperature of 42° C. and remaining bound when subject to washing at 42° C. with 2× SSC buffer at 42° C. Other prefered promoters are capable of hybridizing with the 5' untranslated exon of FIG. 1B: GGATCCCTGCTCCAG-CAGCTGCAAG (SEQ ID NO:3), under the same low stringency conditions.

The subject promoters are isolated from their natural state and are generally incorporated into expression vectors which may be incorporated into cells or transgenic animals for expression and screening, etc. These nucleic acids find a wide variety of applications including use as hybridization probes, PCR primers, therapeutic nucleic acids, etc.; use in detecting the presence of Ob genes and gene transcripts, in detecting or amplifying nucleic acids encoding additional Ob homologs and structural analogs, and in gene therapy applications.

The invention provides efficient methods of identifying pharmacological agents or lead compounds for agents active at the level of Ob gene transcription. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. A wide variety of assays for transcriptional regulators are provided including cell-based transcription assays, promoter-protein binding assays, etc. For example, the disclosed luciferase reporter constructs are used to transfect preadipocytes such as 3T3-L1 cells for cell-based transcription assays. Specifically, the induced adipocytes are plated onto microtiter plates and used to screen libraries of candidate agents for lead compounds which modulate the transcriptional regulation of the Ob gene promoter, as monitored by luciferase expression.

Mapping of the Ob mRNA transcription start site and RACE sequencing:

The transcription start site of the mouse Ob mRNA was determined by primer extension using two antisense oligonucleotide primers, FCT151 and FCT152, complementary to regions close to the 5' end of the mouse leptin open reading frame (ORF). Primer extension was carried out using AMV reverse transcriptase with products resolved on an 8% polyacrylamide electrophoresis gel. 5' RACE (rapid amplification of cDNA ends) analysis was performed using a 5' RACE System Kit (Gibco BRL) following manufacturer's recommendations. Fat tissue from mouse C57BL/6J ob/ob animals was used as an mRNA source to produce first strand cDNA. After first strand synthesis primed using the ob8 oligonucleotide, the mRNA template was degraded using E. coli RNaseH. cDNA was then purified and tailed with dCTP using terminal deoxynucleotidyl transferase. Polymerase chain reaction (PCR) synthesis was then carried out using Taq DNA polymerase, FCT153 and FCT154 primers, coupled with the universal amplification buffer provided by the manufacturer (Gibco BRL). Following amplification the 5' RACE products were cloned into pSPORT1 (Gibco BRL) and sequenced.

Long distance PCR amplification of the Ob gene first exon:

Long distance PCR amplification of mouse genomic DNA was carried out according to the manufacturer's specifications using an XL PCR kit (Perkin Elmer) and primers FCT177 and FCT178. Mouse Ob PCR products identified by Southern blot analysis were subcloned into pSPORT1 (Gibco BRL) and sequenced.

Oligonucleotide primers:

Ob1 5'-AATGTGCTGGAGACCCCTGTG-3' (SEQ ID NO:4)

Ob6 5'-CTTCAGCATTCAGGGCTAACATCCAACTGT-3' (SEQ ID NO:5)

Ob8 5'-AGGTCATTGGCTATCTGCAGCACA-3' (SEQ ID NO:6)

FTC151 5'-AGCCACAGGAACCGACACAGGGGTCT CCAGCACATT-3' (SEQ ID NO:7)

FTC152 5'-ATAGGCACTGCTTGAACATAAGACAGA TAGGACCAA-3' (SEQ ID NO:8)

FTC153 5'-CCGAATTCGCCCAGGAATGAAGTCC AAGCC-3' (SEQ ID NO:9)

FTC154 5'-CCGAATTCCGCCAGTGACCCTCTGC TTGGC-3' (SEQ ID NO:10)

FTC177 5'-CCACGCGTCTGCTCCAGCAGCTGCA-3' (SEQ ID NO:11)

FTC178 5'-CCGCGGCCGCGCACACTGCTTGCTC TTCCAG-3' (SEQ ID NO:12)

FTC180 5'-CCGAATTCCTGCAGCTGTGGGAAACCT AACCATCTC-3' (SEQ ID NO:13)

Isolation of mouse genomic clones:

Genomic clones containing the second and third exons of the mouse Ob gene were obtained by hybridization screening of a bacteriophage lambda library using a PCR amplified probe derived from known Ob-encoding sequences (Zhang et al., 1994). One clone, designated lambda mouse Ob1 (mOb1) was restriction mapped and sequenced at its insert termini, localizing its 5' cloning junction roughly 3.5 kb upstream from the second exon of the Ob gene. A 21 bp primer (FCT178), derived from the sequence located at the 5' terminus of mOb1, was used in combination with a primer (FCT177) derived from the sequence of the 5' RACE clone, to obtain a 3.8 kb PCR product (see above). A hybridization probe was prepared from the 5' end of this long distance PCR product and used to screen a bacteriophage lambda library prepared from C57BL/6 genomic DNA. Overlapping clones spanning 24 kb, including the first, second and third exons of the mouse Ob gene were isolated and mapped by restriction enzyme digestion and Southern blotting according to standard methods (10).

Construction of Ob promoter:luciferase fusion plasmids:

A cloned fragment of the mouse Ob gene encompassing exon 1 was digested with either EcoR1 alone, HindIII and EcoR1, or Asp718 and EcoR1 to yield fragments of roughly 7, 4 and 0.45 Kb. Each fragment contained the same 3' terminus (an EcoR1 site located 142 bp downstream from the first exon) with variable amounts of 5' flanking DNA. These putative promoter fragments were cloned into pGL2-basic (Promega). 5' deletions of the putative mouse Ob promoter were generated by PCR amplification and cloned into pGL2-basic. Site directed mutation of the putative C/EBP response element was introduced by PCR mutagenesis such that the sequence 5'-GTTGCGCAAG-3' (SEQ ID NO:2) was changed to 5'-GCGAATTCGG-3' (SEQ ID NO:14).

Preparation of primary adipocytes and electroporation:

Epididymal fat tissue was excised from two month old mice (C57BL/6J) and prepared for cell culture by collagenase digestion (11). Isolated adipocytes were transfected by electroporation (12) with recombinant Ob-luciferase plasmids and then cultured in DMEM supplemented with 10% fetal bovine serum. Cells were harvested 18 hours post-transfection, lysed and assayed for luciferase enzymatic activity according to manufacturer's recommendations (Promega). All transfections were carried out in duplicate and repeated at least three times.

Tranfection of cultured HepG2 cells:

Transient transfections were carried out using cultured HepG2 cells by the calcium phosphate precipitation method (13). 5 ug of promoter-luciferase plasmid DNA were co-transfected with either 1 ug of pMSV expression vector or 1 ug of pMSV-C/EBPα expression vector. Samples were co-precipitated with 2 ug of salmon sperm DNA and 0.2 ug of a β-galactosidase internal control expression vector, then applied atop adherent HepG2 cells in 6 well tissue culture plates. After 16 hr cells were washed in phosphate buffered saline and refed with fresh DMEM/F12 culture medium supplemented with 10% fetal bovine serum. After an additional 24 hr cells were harvested, lysed and assayed for luciferase and β-galactosidase enzymatic activity according to manufacturer's recommendations (Promega).

Gel mobility shift experiments:

Nuclear extracts were prepared from adipocytes isolated from two month old ob/ob mice (C57BL/6J) according to published procedures (14). Three double-stranded DNA oligonucleotides were used as binding probes in gel mobility shift assays, one corresponding to the presumed C/EBP response element of the Ob promoter, one corresponding to the mutated C/EBP binding site (see above), and one corresponding to an optimal C/EBP binding site (15). Binding assays were carried out according to published procedures (16) using 2 ug of adipocyte nuclear extract. Antiserum to C/EBPα was as described (17).

As a first step towards identification of the mouse Ob promoter, primer extension assays were carried out using two antisense oligonucleotides derived from sequences located close to the 5' terminus of the Ob open reading frame (ORF) (2). As shown in FIGS. 1A-1, -2, both primers predicted the Ob mRNA cap site to be located 56 ribonucleotides 5' to the initiator (ATG) codon of the Ob ORF. This measurement did not correspond to the 115 ribonucleotides predicted from the sequence of the cloned, mouse Ob cDNA (2), consistent with the report that an artifact may have arisen in the generation of the original mouse Ob cDNA clone (18).

In order to resolve the nucleotide sequence corresponding to the 5' terminus of mouse Ob mRNA, 5' RACE methods were used to amplify, clone and sequence the corresponding region. When compared to the sequence of mouse genomic DNA corresponding to the presumed first exon of the Ob gene (2), the 5' RACE sequence diverged from the genomic sequence 31 residues upstream from the ATG codon, leaving approximately 25 residues unaccounted for. It was provisionally assumed that these 25 residues corresponded to a small, untranslated exon.

A mouse genomic clone containing the two coding exons of the Ob gene was obtained (Materials and Methods) and tested by Southern blotting for the presence of the presumptive first exon. Despite containing roughly 3.5 kb of DNA upstream from the first coding exon of the Ob gene, this genomic clone did not contain sequences corresponding to the 5' terminal residues of Ob mRNA (data not shown). The cloning junction of this genomic DNA fragment positioned on the 5' side of Ob coding sequences was sequenced. From this sequence a primer was prepared and used together with a primer derived from the presumed first exon in long distance PCR reactions templated by mouse genomic DNA. The reaction yielded a long distance PCR amplicon of roughly 3.8 kb, which was cloned and sequenced. Such efforts allowed definitive assignment of a small first exon locate roughly 8 kb upstream from the first coding exon of the mouse Ob gene (FIG. 1B).

The DNA sequence of the first exon and upstream DNA of the mouse Ob gene is shown in FIG. 1C. The putative transcription start site is located 25 residues upstream from the first exon/intron boundary and 34 residues downstream from a putative TATA box. A canonical C/EBP response element was identified 15 residues upstream of the TATA box. Given that mRNA coding genes are often preceded by a TATA box (19), and that members of the C/EBP family of transcription factors have been implicated in adipocyte specific gene expression (20), the presence of these putative regulatory regions was consistent with the tentative identification of the Ob gene promoter.

In order to test whether sequences upstream from the small first exon might functionally direct gene expression, various derivatives of the cloned genomic DNA were fused to a luciferase reporter construct and transiently transfected into freshly explanted adipocytes (Materials and Methods). Two promoter constructs were initially tested. One contained 482 bp spanning from an Asp718 restriction site located 458 bp upstream of the transcription start site to the first exon/intron junction (24 bp internal to the Ob gene). The second construct was prepared from the same DNA fragment, yet was altered by site directed mutagenesis to eliminate the putative C/EBP response element (Materials and Methods). When transfected into epididymal fat cells, the native Ob promoter fragment directed the synthesis of between 15 and 20-fold higher levels of luciferase enzyme activity than the promoter-free plasmid (FIG. 2). By contrast, the fragment bearing a mutated C/EBP site failed to direct luciferase levels any higher than the promoter-free control.

The observations summarized in FIG. 2 provide evidence that DNA sequences located upstream from the first exon of the mouse Ob gene can promote transcriptional expression in esplanted adipocytes. They further indicate the function of such sequences may be dependent upon an intact C/EBP response element. In order to further test the potential role of C/EBPα in the functional utilization of the mouse Ob promoter, a variety of promoter constructs were transfected into cultured HepG2 cells, which express little or no C/EBPα protein (21). In this case, duplicate cultures were tested for Ob promoter function in the presence and absence of an expression vector encoding C/EBPα (Materials and Methods). Three constructs were initially tested in HepG2 cells. All were linked to the luciferase promoter via an EcoR1 restriction site located 142 bp downstream from the transcription start site. One extended to an Asp718 restriction site located 458 bp upstream from the gene, and the other two extended to HindIII and EcoR1 sites located roughly 4 and 7 kb, respectively, upstream of the gene.

As shown in FIG. 3A, only the shortest of the three constructs directed the expression of significant luciferase levels in the absence of the C/EBPα expression vector. Upon supplementation of C/EBPα, luciferase expression from this −458 bp (Asp718) construct was elevated 8.7-fold. C/EBPα supplementation also stimulated expression from the two longer constructs. Luciferase activity specified by the 7 kb (EcoR1) fragment was elevated more than 20-fold when supplemented with the C/EBPα expression vector, whereas expression from the 4 kb (HindIII) variant was increased by an 18-fold level.

Figure 3B:
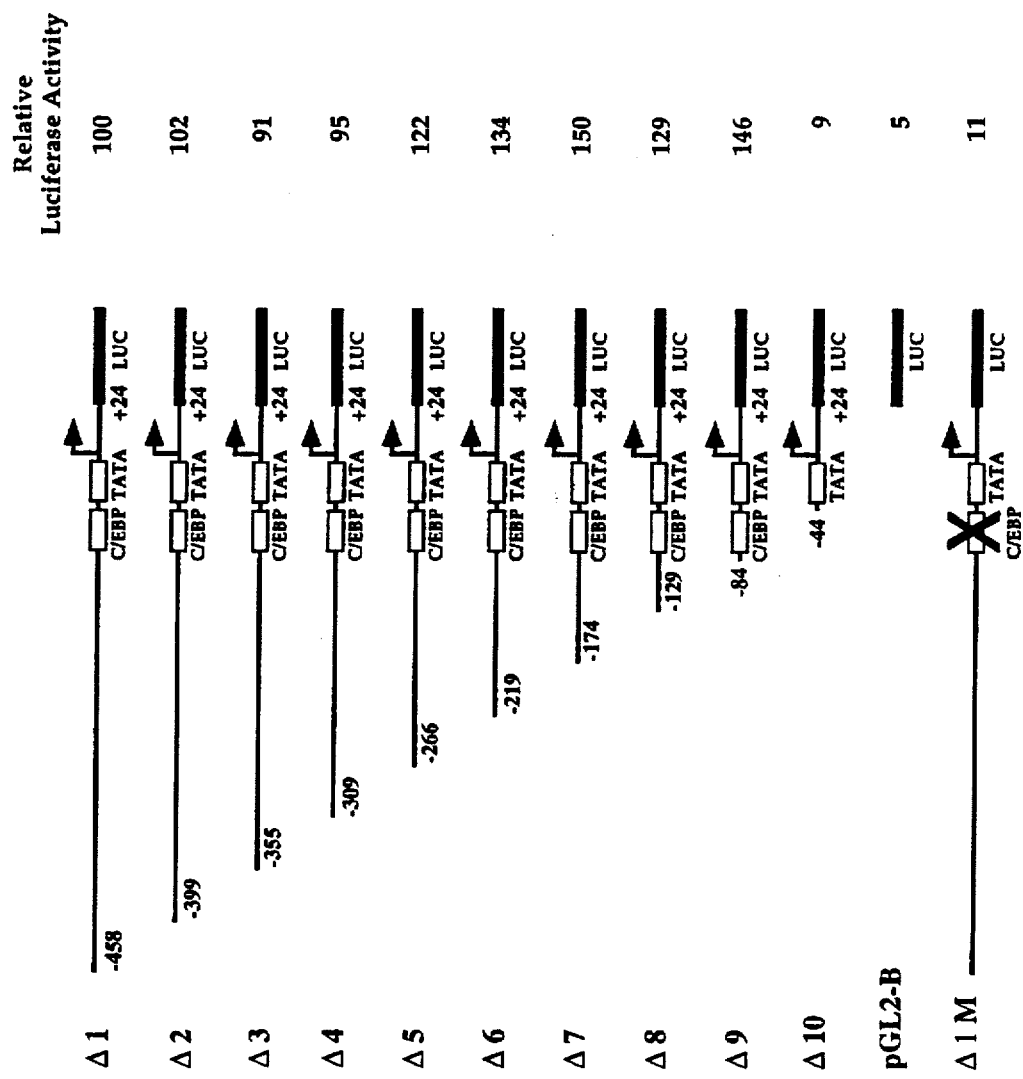

In order to more closely examine elements of the Ob promoter that mediate response to C/EBPα, a series of ten deletion mutants was generated starting with the 458 bp (Asp718) construct. As shown in FIG. 3B, all deleted variants containing an intact C/EBP response element directed the production of comparable luciferase levels in HepG2 cells co-transfected with the C/EBPα expression vector. A deletion mutant missing the C/EBP site was expressed at levels only slightly higher than the promoter-free luciferase vector. Moreover, a derivative of the −458 bp (Asp718) construct that carried a site-directed mutation in the C/EBP response element was similarly defective.

Figure 3C:
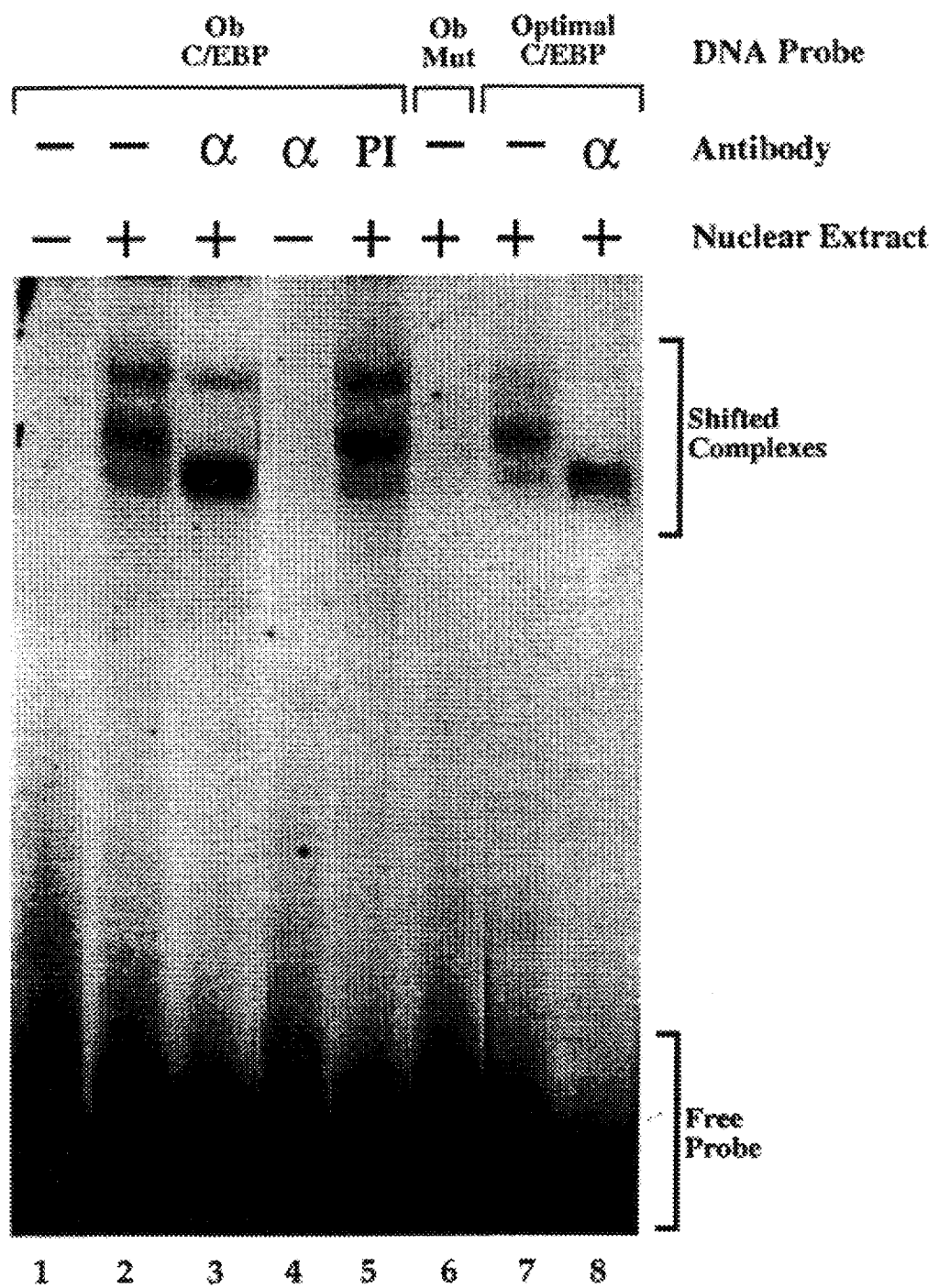

Having obtained provisional evidence for the involvement of C/EBPα in the functional activity of the mouse Ob promoter, gel mobility shift assays were performed using nuclear extracts prepared from freshly explanted epididymal adipocytes. Double stranded oligonucleotides were synthesized corresponding to the C/EBP response element of the Ob promoter, the mutated version tested in transient transfection assays (see FIGS. 2 and 3), and a known, optimal C/EBP response element (15). The radiolabeled probes were mixed with adipocyte nuclear extract and subjected to electrophoresis on non-denaturing electrophoresis gels. Co-migrating, shifted complexes were observed for the known C/EBP binding site as well as that derived from the native Ob promoter, yet were not observed for the mutated variant (FIG. 3C).

Antiserum specific to C/EBPα eliminated the predominant complex, yet did not generate any artifactual mobility shift when applied in the absence of added nuclear extract. It is notable that treatment of adipocyte nuclear extracts with antiserum to C/EBPα resulted in enhanced binding by the most rapidly migrating band observed in untreated extracts. Since the pattern of gel-shifted complexes was not altered by non-immune serum, this enhanced band may represent a C/EBP-like protein that was not purged upon antibody treatment. It may represent the smaller, 30 Kd translation product of C/EBPα mRNA (22) or one of the other members of the C/EBP family of transcription factors (16). Finally, the sizes of the complexes formed on the Ob C/EBP response element, as well as the sensitivity of these binding activities to C/EBPα antiserum, were indistinguishable from a known, high-affinity C/EBP binding site (15).

Isolation of human Ob gene promoter and functional assay:

Data obtained from the murine Ob gene promoter were used to identify the corresponding human Ob gene promoter. Briefly, a human genomic DNA library was prepared from human genomic DNA isolated from primary cells (peripheral blood lymphocytes) and packaged into lamda phage. This library was probed with radiolabeled 5′ untranslated RACE product (prepared from oligonucleotides derived from the a human Ob ORF, Genbank). Hybridizing clones were subject to Southern blot analysis to generate a restriction map of overlapping lamda clones, which localized the corresponding 5′-most untranslated exon of the human Ob gene. The overlapping clones were sequenced and compared with the corresponding murine promoter sequences. Based on sequence similarity, a putative human Ob gene promoter was identified. C/EBP transcriptional dependency of the putative promoter using a luciferase reporter as described above confirms its functionality as a human Ob gene promoter.

The following examplary binding assay is offered by way of illustration and not by way of limitation.

Protocol for C/EBP-Ob Gene Promoter Binding Assay

A. Reagents:

Neutralite Avidin: 20 μg/ml in PBS.

Blocking buffer: 5% BSA, 0.5% Tween 20 in PBS; 1 hr. RT.

Assay Buffer: 100 mM KCl, 20 mM HEPES pH 7.6, 0.25 mM EDTA, 1% glycerol, 0.5 % NP-40, 50 mM BME, 1 mg/ml BSA, cocktail of protease inhibitors.

$^{33}$P C/EBP 10× stock: $10^{-6}$–$10^{-8}$M "cold" C/EBP supplemented with 200,000–250,000 cpm of labeled C/EBP (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

Oligonucleotide stock: (specific biotinylated). Biotinylated oligo at 17 pmole/μl, Ob gene promoter containing C/EBP binding site: (BIOTIN)-GACAGTTGCGCAAGTGGACT B. Preparation of assay plates:

Coat with 120 μl of stock N-Avidin per well overnight at 4° C.

Wash 2× with 200 μl PBS.

Block with 150 μl of blocking buffer.

Wash 2× with 200 μl PBS.

C. Assay:

Add 40 μl assay buffer/well.

Add 10 μl compound or extract.

Add 10 μl $^{33}$P-C/EBP (20,000–25,000 cpm/0.1–10 pmoles/well=$10^{-9}$–$10^{-7}$M final concentration).

Shake at 25 C for 15 min.

Incubate additional 45 min. at 25 C.

Add 40 μl oligo mixture (1.0 pmoles/40 ul in assay buffer with 1 ng of ss-DNA)

Incubate 1 hr at RT.

Stop the reaction by washing 4× with 200 μl PBS.

Add 150 μl scintillation cocktail.

Count in Topcount.

D. Controls for all assays (located on each plate):

a. Non-specific binding (no oligo added)

b. Specific soluble oligo at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated nucleic acid comprising a sequence from −458 to +147 of a natural murine ob gene, or a terminal deletion mutant thereof sufficient to promote preferential transcriptional expression in an adipocyte.

2. A nucleic acid according to claim 1 wherein said deletion mutant comprises −44 to +24 of a native ob gene.

3. A nucleic acid according to claim 1 comprising a C/EBP binding site comprising the sequence: GTTGCG-CAAG.

4. A nucleic acid according to claim 1 comprising an untranslated first exon of said ob gene.

5. A nucleic acid construct comprising a nucleic acid according to claim 1 operatively linked to a reporter gene.

6. A cell comprising the construct of claim 5.

7. A method of screening for a candidate, agent which modulates the transcriptional regulation of the ob promoter, said method comprising:

assaying reporter gene expressions in a cell according to claim 6 in the presence and absence of the candidate agent, wherein a difference between the expressions indicates the agent modulates the transcriptional regulation of the ob promoter.

* * * * *